(12) United States Patent
Widlund (10) Patent No.: US 7,368,627 B1
(45) Date of Patent: May 6, 2008

(54) ABSORBENT ARTICLE HAVING IMPROVED SURFACE PROPERTIES

(75) Inventor: Urban Widlund, Pixbo (SE)

(73) Assignee: SCA Hygiene Products AB, Goteborg (SE)

( * ) Notice: Subject to any disclaimer, the term of this patent is extended or adjusted under 35 U.S.C. 154(b) by 0 days.

(21) Appl. No.: 09/194,700

(22) PCT Filed: Feb. 3, 1998

(86) PCT No.: PCT/SE98/00187

§ 371 (c)(1),
(2), (4) Date: Mar. 4, 1999

(87) PCT Pub. No.: WO98/33463

PCT Pub. Date: Aug. 6, 1998

(30) Foreign Application Priority Data

Feb. 4, 1997 (SE) .................................... 9700371

(51) Int. Cl.
*A61F 13/15* (2006.01)
*A61F 13/20* (2006.01)

(52) U.S. Cl. .............................. 604/378; 604/385.101; 604/385.01; 604/367

(58) Field of Classification Search ................ 604/540, 604/385.08, 385.17, 358, 367–378, 381–382, 604/385.01
See application file for complete search history.

(56) References Cited

U.S. PATENT DOCUMENTS

| | | | | |
|---|---|---|---|---|
| 3,559,649 A | * | 2/1971 | Grad et al. .................. 604/382 |
| 3,768,118 A | * | 10/1973 | Ruffo et al. ................ 19/156.3 |
| 3,799,167 A | * | 3/1974 | Miller et al. ................. 604/382 |
| 3,837,343 A | * | 9/1974 | Mesek .......................... 128/284 |
| 3,838,692 A | * | 10/1974 | Levesque ..................... 604/381 |
| 4,627,847 A | * | 12/1986 | Puletti et al. ................ 604/366 |
| 4,631,062 A | * | 12/1986 | Lassen et al. ........... 604/385.02 |
| 5,300,055 A | | 4/1994 | Buell ........................ 604/385.1 |
| 5,330,456 A | * | 7/1994 | Robinson ..................... 604/368 |
| 5,449,352 A | * | 9/1995 | Nishino et al. .............. 604/383 |
| 5,545,156 A | * | 8/1996 | DiPalma et al. .......... 604/385.1 |
| 5,562,650 A | | 10/1996 | Everett et al. .............. 604/378 |
| 5,591,150 A | * | 1/1997 | Olsen et al. .............. 604/685.1 |
| 5,681,300 A | | 10/1997 | Ahr et al. .................... 604/367 |
| 5,885,268 A | * | 3/1999 | Bien et al. ............. 604/385.01 |
| 6,183,847 B1 | * | 2/2001 | Goldwasser ................ 428/219 |

FOREIGN PATENT DOCUMENTS

EP 0 747 029 A1 12/1996

(Continued)

*Primary Examiner*—Michele Kidwell
(74) *Attorney, Agent, or Firm*—Buchanan Ingersoll & Rooney PC (57) ABSTRACT

An absorbent article has a liquid pervious user-facing first side including a liquid-pervious surface layer composed of hydrophobic material, a second side opposite the first side and including a liquid-impervious surface layer, and an absorbent body enclosed between the two surface layers. The first side further exhibits a wetting region, which is the region of the first side intended to first be wetted by body fluid emitted to the article. The wetting region is constituted of a hydrophilic material. An outer edge portion of the wetting region is bordered by the hydrophobic material of the liquid pervious surface layer which is situated laterally outwardly of the wetting region.

3 Claims, 3 Drawing Sheets

FOREIGN PATENT DOCUMENTS

| WO | WO 94/10953 | 5/1994 |
| WO | WO 94/10956 | 5/1994 |
| WO | WO 9409737 | 5/1994 |
| WO | WO 95/11649 | 5/1995 |
| WO | WO 96/27351 | 9/1996 |
| WO | WO 98/22057 | 5/1998 |
| WO | WO 98/22058 | 5/1998 |
| WO | WO 98/22061 | 5/1998 |

* cited by examiner

ABSORBENT ARTICLE HAVING IMPROVED SURFACE PROPERTIES

TECHNICAL FIELD

The invention pertains to an absorbent article intended for female users, such as a sanitary napkin, a panty-liner, or an incontinence protector, comprising a liquid-pervious first side, a liquid-impervious second side, and an absorbent body enclosed between the two sides, wherein the article further exhibits a wetting region, which is the region of the liquid-pervious first side which is intended to first be wetted by body fluid emitted to the article.

BACKGROUND OF THE INVENTION

Certain types of absorbent articles such as sanitary napkins and incontinence protectors for lightly incontinent female users are intended to be worn in close contact against the body of the user. Such an absorbent article is thereby usually applied inside the panties of the user and is kept in contact against the body by the pressure from the panties during use.

It is important that the surface of an absorbent article which is intended to be facing the body of the user is soft and comfortable and does not cause irritation. Furthermore, the surface of the article should have the ability to receive the body fluid which is emitted to the article, and rapidly let the liquid pass into the article and be absorbed by it. If the liquid is not admitted into the article sufficiently quickly, the risk is obvious that the liquid instead will flow onto the surface of the article and cause leakage. Furthermore, the surface of the article will become wet and sticky, something which is perceived as extremely unpleasant by a majority of users. A wet surface may further cause the user inconvenience in the form of skin irritation.

In order to avoid wet surfaces on absorbent articles, these are generally provided with a liquid-pervious surface layer of a comparatively hydrophobic material. Examples of such hydrophobic materials are perforated plastic films, plastic scrims and nonwoven materials of hydrophobic fibres. The term nonwoven material refers to different types of nonwoven, bonded fibre layers. Such hydrophobic layers have a very low wettability and are therefore usually treated, for example, with surfactants in order to increase the wettability and the ability to admit liquid through. In spite of this, the acquisition rate of hydrophobic surface materials is often too low.

The hydrophobic surface layers exhibit a very dry surface, even after wetting. However, small liquid quantities may remain in or on the surface layer after wetting, since the liquid transportation ability in a hydrophobic surface layer is low. It is true, for instance, that a perforated plastic layer has good liquid transportation ability through the perforations, but liquid which has ended up between the perforations tends to remain on the surface.

Remaining liquid in or on the liquid-pervious surface layer constitutes a problem, in particular when the absorbent article is a sanitary napkin, since menstrual fluid has a relatively high viscosity and thereby has a larger inclination to leave residues on the liquid-pervious cover layer. Such remaining liquid results in the surface of the sanitary napkin becoming wet and sticky, which is a disadvantage both during use and when the sanitary napkin shall be replaced.

Since an absorbent article, such as a sanitary napkin or an incontinence protector, usually is attached inside the panties of the user by adhesive surfaces arranged on the article, the article follows the movements of the panties during use. This implies that the position of the article is changed somewhat in relation to the body of the user when the user moves about. In this way, liquid which has remained on the surface of the article will be smeared out across the surface. The soiled surface bears on the body of the user, something which of course is perceived as unpleasant and insanitary.

Absorbent articles for female users are sometimes provided with a hump, intended to be arranged in the genital region of the user during use, in order to catch body fluid as soon as it leaves the body of the user. Such a hump may thereby completely, or partially, be placed between the labia pudendi of the user, and will thereby come into contact with the mucous membranes inside the labia pudendi. Thereby, it has been found that the, proportionately, very dry surface on a conventional hydrophobic surface layer can cause discomfort in the form of chafing and irritation of the mucous membranes.

By means of the present invention, however, an absorbent article has been achieved with which the problems associated with previously known such articles essentially have been eliminated. Accordingly, by means of an article according to the invention it is possible to offer both a dry surface against the skin of the user, rapid liquid acquisition and minimal irritation of the mucous membranes of the user.

An article designed in accordance with the invention is primarily characterized in that the wetting region of the user-facing side of the article is constituted of a hydrophilic absorbent material, at least at a surface of the article which is intended to be facing the user during use, and in that the remaining parts of the user-facing side of the article are constituted of a hydrophobic material.

The hydrophilic portion of the user-facing side may come into contact with the mucous membranes of the user in the genital region during use. Since the hydrophilic material is able to retain moisture, desiccation of the mucus membranes is counteracted.

Advantageously, the hydrophilic material has a certain absorbency of its own, so that liquid is not only absorbed into the voids of the material, but also into the material itself. For instance, it is suitable to use a fibre material in which at least some of the integral fibres have the ability to absorb liquid into the fibres. Thereby, the risk that the hydrophilic material is entirely drained of liquid by underlying absorption material is non-existent. Accordingly, such an absorbent material will maintain a wet surface bearing on the mucous membranes of the user during use.

The article, according to the invention, may advantageously be provided with a hump, projecting from the user-facing side, wherein the location of the hump on the article at least partially coincides with the wetting region. By means of arranging a hump at the wetting region, it is ensured that the hydrophilic region of the article is in contact against the mucous membranes of the user during use and prevents desiccation of these. Preferably, the hump is shaped in such a way that it conforms to the body shape of the user in the region in question, whereby the risk of placing the article in the wrong position is minimal. An anatomically correct design of a hump on the article contributes moreover to the article being directed into and being kept in the correction position in relation to the genitals of the user.

A hump of the herein intended type may, for example, be achieved by means of the absorbent article comprising shaping members which, through the action of the forces which the article is subjected to during use, have the ability to bring the wetting region of the article into contact with the mucous membranes of the user. Such shaping members may, for example, be constituted of compressions, folding notches or the like, or of a deformable insert.

The hydrophilic material in the liquid-pervious surface layer may, for example, primarily consist of hydrophilic, absorbent fibres such as cellulose fibres, cotton, rayon, jute, peat moss, or the like. Alternatively, the hydrophilic material in the liquid-pervious surface layer may primarily consist of hydrophilic absorbent foam material, such as polyurethane foam, cellulose foam, or the like.

The hydrophobic material in the liquid-pervious surface layer may, for example, primarily consist of hydrophobic fibres such as polypropylene fibres, polyethylene fibres, polyester fibres, or hydrophobic bi-component fibres, or of a hydrophobic foam material, such as polyethylene foam.

Although it is preferred, the liquid-pervious surface layer does not have to be composed of different components, but may consist of one and the same material layer, which has been treated so that it has different properties within different regions of its surface. Accordingly, the hydrophilic material in the liquid-pervious surface layer may be constituted of a hydrophobic material which has been rendered hydrophilic. In a corresponding way, the hydrophobic material in the liquid-pervious surface layer may of course be constituted of a hydrophilic material which has been rendered hydrophobic.

A number of different types of treatment for modifying the surface and changing the surface properties of materials for absorption purposes are well-known to the person skilled in the art. The most common way to achieve hydrophilicity for an initially hydrophobic material, is to treat the material with a wetting agent. The largest disadvantage of treatment with a wetting agent, however, is that the wetting agent gradually is flushed out of the material, whereafter this returns to its initial hydrophobic state. Also other methods for rendering a hydrophobic material hydrophilic are previously known, such as flame treatment, corona or plasma.

According to one embodiment of the invention, the liquid-pervious user-facing side comprises a laminate of a first liquid-pervious, hydrophobic material layer, arranged closest to the absorbent body, and a second liquid-pervious, hydrophilic material layer of substantially the same extension as the wetting region of the article, and intended to bear on the body of the user in the wetting region during use.

According to another embodiment of the invention, the liquid-pervious user-facing side comprises a laminate of a first liquid-pervious, hydrophobic material layer, and a second liquid-pervious, hydrophilic material layer arranged closest to the absorbent body, inside the first material layer, wherein the hydrophobic material layer exhibits an opening of substantially the same extension as the wetting region of the article through which the hydrophilic layer is exposed.

It is an advantage if the absorbent article is kept in position against the body of the user without being attached to the underwear of the user. The article may thereby, for instance, have such a shape and stiffness that it remains in position against the body of the user without the need for a special attachment member. Suitably designed articles are described in, for example, SE 9604224-7, SE 9604222-1 and SE 9604223-9. Alternatively, the article may be kept in position against the body of the user by means of a girdle, or the like, which is detached from the panties.

Particularly when such articles which initially are essentially planar are concerned, it may be suitable to provide the article with some kind of shaping member which, preferably by means of influence of the forces which the article is subjected to during use, has the ability to bring the wetting region into contact with the mucous membranes of the user.

Examples of such shaping members are folding notches, such as compressions or slits, and stiffening inserts, with or without hinge-like portions. Furthermore, it is possible to use different types of elastic means or elements which the user herself bends or forms in another way before use.

BRIEF DESCRIPTION OF THE DRAWINGS

In the following, the invention will be described with reference to the embodiments shown in the attached drawings, in which.

DETAILED DESCRIPTION OF PREFERRED EMBODIMENTS

Figure 1:
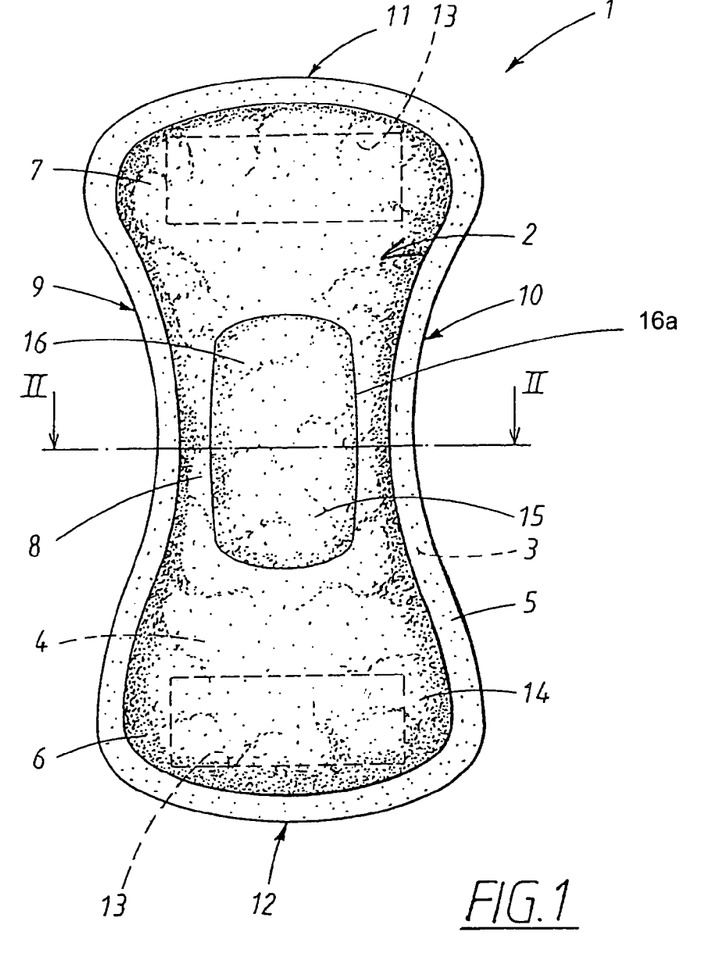
FIG. 1 shows a sanitary napkin according to a first embodiment of the invention.
Figure 2:
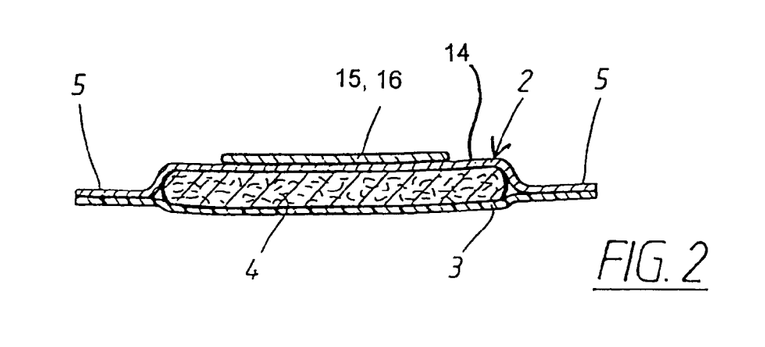
FIG. 2 shows a section along the line II-II through the sanitary napkin in FIG. 1.

The sanitary napkin 1 shown in FIGS. 1 and 2 comprises a user-facing liquid-pervious first side 2, composed of first and second layers 14, 16, which is intended to be facing the user during use, a liquid-impervious layer surface layer 3 defining an opposite second side of the sanitary napkin which is intended to be facing away from the user during use, and an absorbent body 4 enclosed between the layers 14, 3. The layers 14, 3 have essentially the same shape as the absorbent body 4, but a slightly larger extension in the plane, whereby they form a protruding edge 5 around the entire periphery of the absorbent body 4. The layers 14, 3 are mutually connected within the protruding edge 5, for example by gluing, sewing, or welding by means of heat or ultrasonics.

The liquid-impervious surface layer 3 is of a conventional type and may, accordingly, consist of any liquid-impervious material suitable for the purpose. Examples of such materials are different types of thin plastic films or nonwoven materials which have been treated in order to resist liquid penetration, for example by means of coating with plastic, wax, or the like. The liquid-impervious surface layer 3 may further be constituted of a liquid-impervious surface on the absorbent body 4.

The absorbent body 4 consists of one or several layers of absorbent material such as cellulose fluff pulp, absorbent bonded fibre layers, tissue layers, absorbent foams, peat moss, or the like. The absorbent body may further contain superabsorbent polymers, i.e. polymers with the ability to absorb several time their own weight of liquid during the formation of liquid-containing gel. Superabsorbents are usually present in the form of particles, flakes, fibres, granules, or the like. The superabsorbent material may occur alone, or in combination with other absorbent material.

The sanitary napkin 1 is hourglass-shaped with wider end portions 6, 7 and a narrower crotch portion 8 between the end portions 6, 7. The sanitary napkin 1 further exhibits two longitudinal, concavely-curved side edges 9, 10 and two transverse convexly-curved end edges 11, 12.

An attachment member 13, in the form of a region of self-adhesive glue, is arranged on the outside of the liquid-impervious surface layer 3 at each end portion 6, 7 of the sanitary napkin 1. During use, the sanitary napkin 1, this is applied inside the panties of the user and is attached to the panties by means of the attachment member 13. Before use, the attachment member 13 is protected in a conventional way, for example by means of being covered by a protective layer of paper or plastic which has been treated with silicone, or embossed in order to be easily detachable from the glue when the sanitary napkin is to be used. Alternatively, the glue may of course be arranged in any pattern suitable for the purpose such as longitudinal strands, complete coverage, or the like. Furthermore, other types of attachment members may be used, such as frictional coverings, snap fasteners, clamps, attachment flaps, or the like.

The liquid-pervious first layer 14 consists of conventional, hydrophobic liquid-pervious material. The first layer 14 is applied over the surface on the absorbent body 4 which is intended to be facing the user during use. Examples of hydrophobic surface materials are perforated plastic films, hydrophobic nonwoven materials, plastic scrims, or the like. A hydrophobic surface material admits liquid through to the underlying absorbent body 4. Since the absorbent body is more hydrophilic than the material in the first layer 14, the layer 14 is almost completely drained of liquid after wetting. For this reason, and since the first layer 14 essentially lacks absorbency, the layer 14 remains dry even after wetting. Only a very small liquid quantity may remain on or inside the surface layer 14.

During use, the sanitary napkin 1 is applied in the genital region of the user, with the crotch portion 8 of the sanitary napkin located at the urethra opening and the vaginal opening of the user. By means of this, emitted body fluid will hit the sanitary napkin 1 within a limited area on the user-facing first side 2 of the sanitary napkin, the so-called wetting region 15 occupied by the hydrophilic and absorbent second layer 16. Thereby, examples of suitable, hydrophilic materials are absorbent, bonded cellulose layers, nonwoven materials and woven, knitted or crocheted textile materials, entirely or primarily consisting of hydrophilic fibres such as cotton, cellulose, rayon, peat moss, or the like. Since the hydrophilic material may come into contact with the mucous membranes in the genital region of the user during use, it is extremely important that the material is skin-friendly and does not contain any component which may cause allergic reactions, or other troubles.

Instead of using a special hydrophilic second layer 16, it is of course possible to achieve a hydrophilic region by means of treating the first, first layer 14 with a wetting agent, or any other type of surface-modifying treatment within the wetting region 15 of the sanitary napkin. Thereby, it is essential that the treated region has the ability to retain at least a small liquid quantity after wetting so that the mucous membranes of the user are kept moist when they are in contact with the wetting region 15 of the sanitary napkin.

The second layer 16 may come into contact with the sensitive mucous membranes inside the labia pudendi of the user during use. Since the second layer 16 is hydrophilic and absorbent, there is no risk of desiccation of the mucous membranes, since part of the liquid which is absorbed by the sanitary napkin will stay in the second layer 16. Thereby, the mucous membranes are kept moist during use, and the risk of chafing and other irritation of the mucous membranes is almost entirely eliminated. Furthermore, the risk of liquid flowing onto the surface of the article before it is absorbed into the article is very small, since the hydrophilic, second layer 16 has high wettability and immediately catches and absorbs emitted body fluid.

In contrast to the mucous membranes, the skin of the user in the genital region should be protected against wetting. Within the portions of the surface of the sanitary napkin 1 which are in contact with the skin of the user during use, therefore only the hydrophobic first layer 14 is present. Thereby, a high dryness against the skin is achieved, and irritation of the same is avoided.

During normal use of the sanitary napkin, i.e., at moderate liquid flows and on condition that the sanitary napkin is correctly positioned in relation to the body of the user, the first surface layer 14 will not primarily be wetted by liquid. The liquid which is emitted will instead first hit the second hydrophilic layer 16 and thereafter be absorbed further into the absorbent body 4 where the liquid is distributed. Because of its low wettability, the first, hydrophobic layer 14 serves as a barrier against passage of liquid back out from the sanitary napkin. This implies that also a sanitary napkin which has absorbed a relatively large amount of liquid feels dry against the skin in the regions which surround the wetting region 15 of the sanitary napkin.

Another advantage with arranging the hydrophobic layer 14 inside the hydrophilic layer 16, so that an outer edge portion 16a of the wetting region 15 is bordered by the hydrophobic material of the layer 16 situated laterally outwardly of the wetting region, is that the transport into the absorbent body 4, of the liquid which is emitted to the sanitary napkin, is braked by the hydrophobic layer 14. This implies that the effect of the outer, hydrophilic layer 16 is magnified, since liquid more easily remains in this layer and is not drained into the absorbent body as easily as if the hydrophilic layer 16 had been in direct contact with the absorbent body 4.

Figure 3:
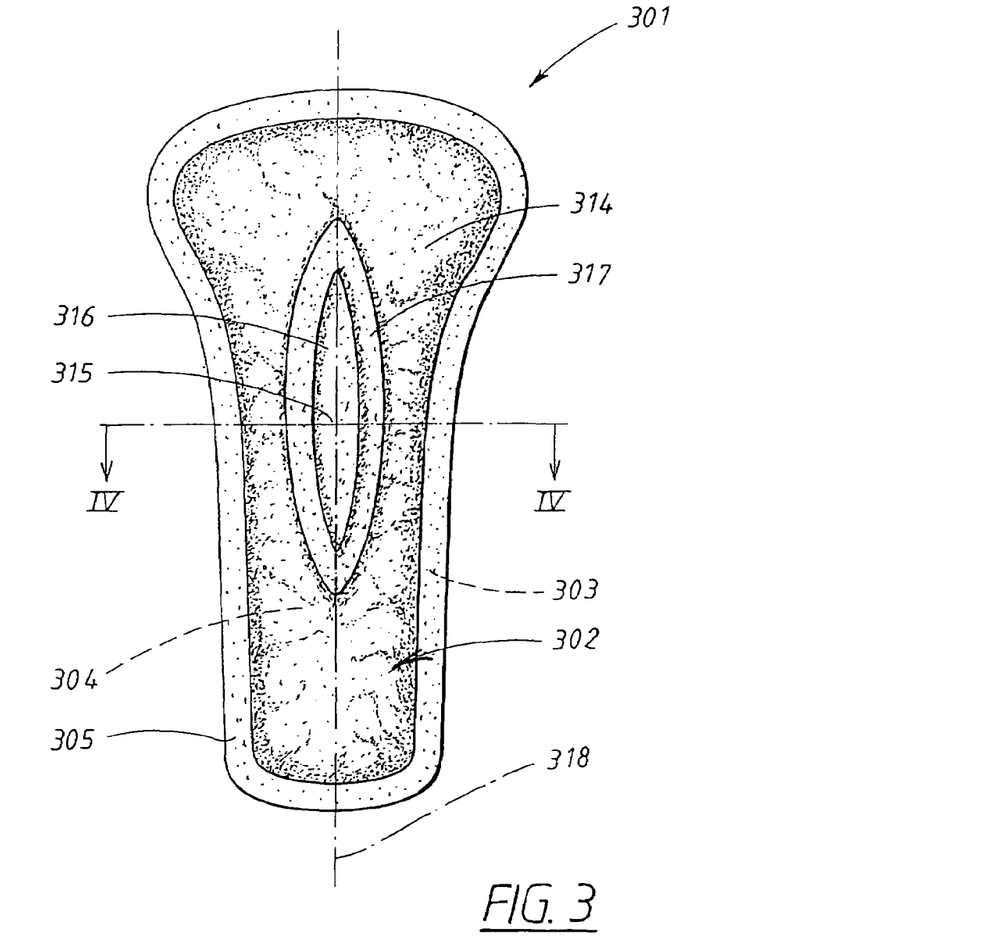
FIG. 3 shows a sanitary napkin according to a second embodiment of the invention.
Figure 4:
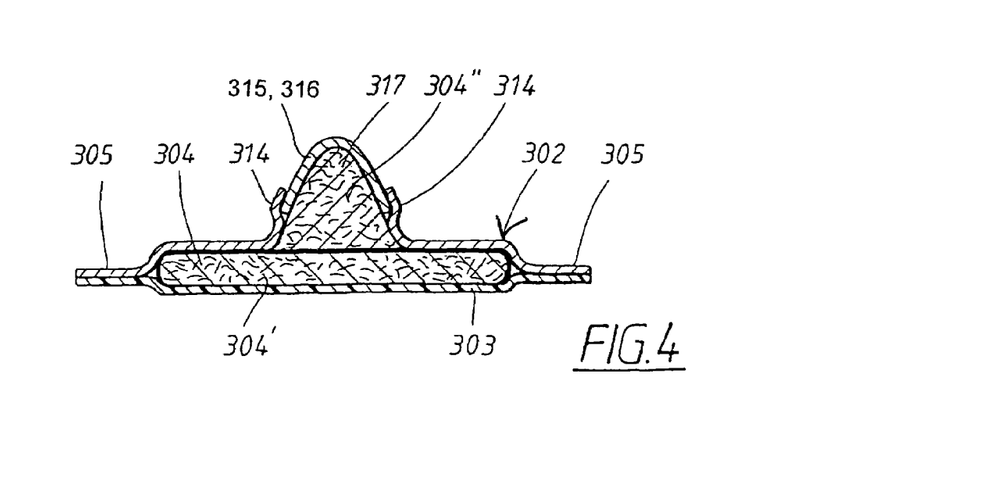
FIG. 4 shows a section along the line IV-IV through the sanitary napkin in FIG. 3.

In FIGS. 3 and 4 another sanitary napkin 301 is shown, with the same basic construction as the sanitary napkin 1 shown in FIGS. 1 and 2. Accordingly, the user-facing first side 302 of the sanitary napkin in FIGS. 3 and 4 exhibits a liquid-pervious first layer 314, a liquid-impervious surface 303, and an absorbent body 304 disposed between the surface layers 314, 303. The surface layers 314, 303 are mutually connected along an edge portion 305, protruding around the absorbent body 304.

The absorbent body 304 consists of two parts, of which a first part 304' is located closest to the liquid-impervious surface layer 303, and a second part 304" forms a longitudinal hump 317, which extends upwardly past the first layer 314 and along the longitudinal centre line 318 of the sanitary napkin.

The liquid-pervious first side 302 consist of two parts, of which the first part is constituted by the first layer 314, which is hydrophobic and essentially lacks absorbency of its own. The second part is constituted by a second layer 316 which is hydrophilic, with a certain absorbency of its own. The second layer 316 is arranged at the wetting region 315 of first side of the sanitary napkin which coincides with a longitudinal central portion of the hump 317. Since the hump 317 is intended to penetrate a small distance in between the labia pudenda of the user during use and separate these a little, the wetting region 315 will be in contact with the mucous membranes inside the labia pudenda during use. For this reason, it is important that the layer 316 in the wetting region 315 is not so dry that the hump 315 chafes or in another way irritates the mucous membranes.

The presence of the hump 317 is extremely advantageous, since the hump 317 improves the fit of the sanitary napkin and makes it possible to almost exactly predict which region which will bear on the mucous membranes of the user during use. Thereby, it is possible to restrict the hydrophilic portion of the surface of the sanitary napkin solely to this region, and thereby to achieve a sanitary napkin with a surface which otherwise is dry and pleasant against the skin of the user. In this respect it is of no significance if the hump is preformed, such as shown in FIGS. 3 and 4, or is formed during use by means of the absorbent article comprising some type of shaping member which, through the influence of the forces which arise during use, guides the formation of a hump on the surface of the article.

The sanitary napkin lacks a special attachment member, since the pressure from the panties of the user, together with the hump bearing closely on the body, implies that the sanitary napkin is displaced comparatively little in relation to the body of the user during use. However, it is possible to provide the sanitary napkin with any known type of attachment member, if this is found to be desirable. However, attachment members which keep the sanitary napkin against the body independently of the movements of the underwear of the user are preferred.

Figure 5:
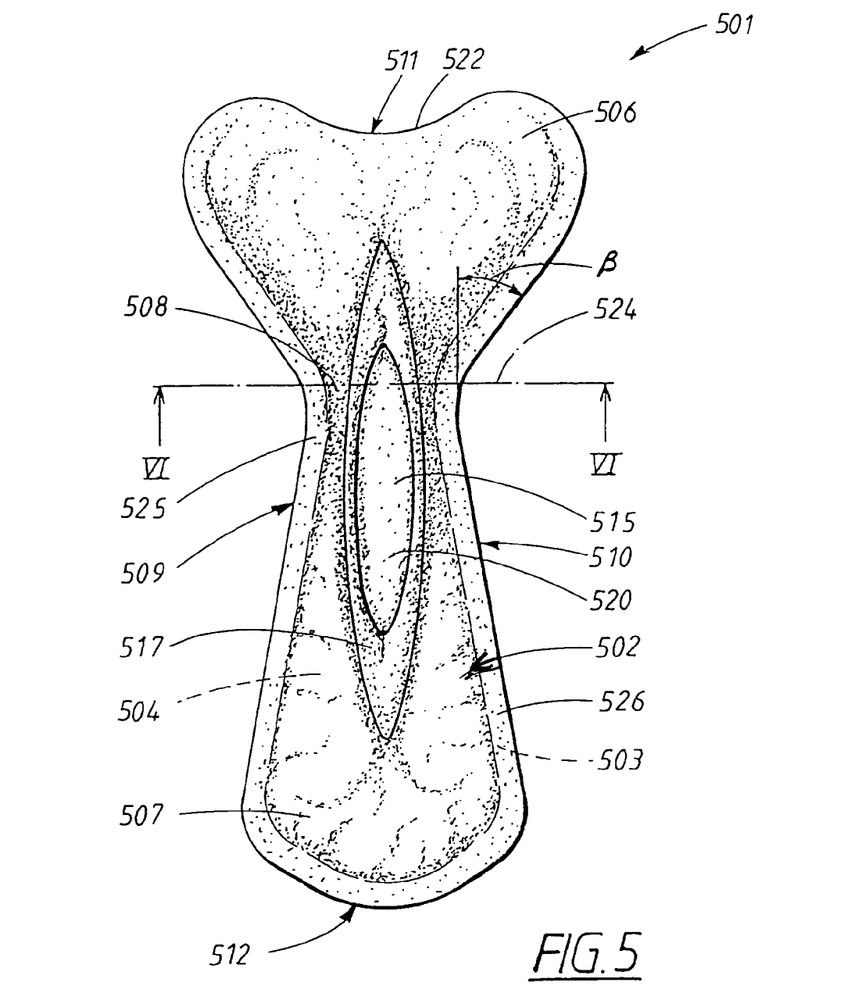
FIG. 5 shows a sanitary napkin according to a third embodiment of the invention and FIG. 6 shows a section along the line VI-VI through the sanitary napkin in FIG. 5.
Figure 6:
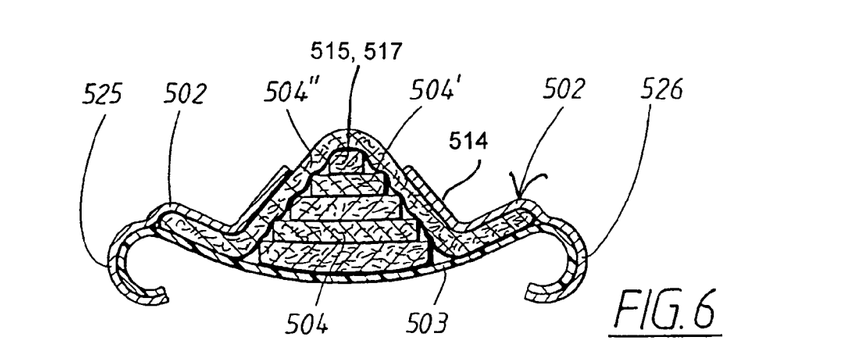

The sanitary napkin 501 shown in FIGS. 5 and 6 has a construction which is somewhat different from the construction of the earlier described sanitary napkins 1, 301. The sanitary napkin 501 comprises a liquid-pervious user-facing first side 502, a liquid-impervious surface layer 503, and an absorbent body 504 therebetween. The liquid-impervious surface layer 503 is constituted of a thick, rigid plastic layer, which forms a hard, shape-permanent shell onto which the absorbent body 504 is arranged.

The sanitary napkin 501 is shaped with a front portion 506, which is wider than the rear portion 507, and with a crotch portion 508 which is narrower than both the front portion and the rear portion. Since the liquid-impervious cover layer 503 is so rigid, it is essential that the sanitary napkin has a shape which to a very high extent is adapted to the anatomy of the user. Thereby, it is of particularly great significance that the width of the sanitary napkin, at least within a portion of the crotch portion 508, does not exceed 30-35 mm, or is compressible to approx. 30-35 mm. It has, namely, been found that there is a critical area in the groin area of all users where the distance between the muscles travelling down along the thighs is approximately 30-35 mm. A very rigid sanitary napkin with a width which exceeds the distance between the muscles in the critical area, will press and chafe against the inside of the legs of the user during use. Therefore, it is essential that at least part of the crotch portion 508 has a width which without any discomfort can be accommodated in the critical area.

The sanitary napkin 501 further exhibits two longitudinal side edges 509, 510, a transverse concavely-curved front edge 511 and a transverse, convexly-curved rear edge 512. The sanitary napkin is shaped in such a way that, in the front part of the crotch portion 508, there is a cross-sectional line 524, extending in the transverse direction of the sanitary napkin, which intersects the side edges 509, 510 the sanitary napkin, wherein the side edges 509, 510 change inclination in relation to the longitudinal centre line 518 of the sanitary napkin at the cross-sectional line 524. The width of the sanitary napkin increases in a direction from the cross-sectional line 524 towards the front edge 511, whereby the front portion 506 exhibits a maximum width which exceeds the width of the crotch portion 508 at the cross-sectional line 524. Thereby, the maximum width of the front portion 506 is at least twice the width of the crotch portion 508 at the cross-sectional line 524. The inclination of the side edges 509, 510 at the front portion 506 is defined by an angle β between each respective side edge 509, 510 and a longitudinal line parallel to the centre line 523, wherein β is between 30° and 90° and wherein the width of the crotch portion 508 at the cross-sectional line 524 is between 15 and 45 mm and preferably between 20 and 40 mm.

The absorbent body 504 comprises a first part 504', which forms a longitudinal hump 517 on the side of the sanitary napkin which is intended to be facing a user during use. The first part 504' consists of several layers of a material with high absorbency, stacked onto each other, wherein the size of the layers decreases in a direction towards the top of the hump 517. Thereby, the hump 517 obtains an anatomically correct shape, tapering towards the top. An absorption material, particularly suited for the purpose, is the fibre material which is disclosed in Wo 94/10953 and WO 94/10956. These materials occur in the form of dry-laid fibre layers, having high density and stiffness, and are use directly in an absorbent article without first being defibered. A hump built up from such material has high stiffness and good ability to resist pressure deformation, whereby the central hump 517 exhibits an excellent shape permanence. Furthermore, the fibre material has a high absorption capacity. During absorption, the material swells slightly in the thickness direction, and the hump thereby conforms to the available space in the genital region of the user. An advantage with this is that the hump 517 adopts a shape which is uniquely adapted to each user. In this way, both the leakage security and the user comfort are increased.

It is of course possible to use other types of absorption materials, such as absorbent foams, or absorbent fibres such as cellulose fluff pulp, rayon, peat moss, cotton or the like with or without superabsorbent material. All conceivable combinations and mixtures of absorbent materials can be used. Furthermore, it is not necessary that the first part 504' of the absorbent body 504 is constituted of the shown layer structure. Accordingly, the first part 504' may consist of a single piece of absorption material, for example a foam, or a formed fibre wadding, or material layers placed in the height direction, rolled up, or the like.

The absorbent body 504 of the sanitary napkin 501 further comprises an absorption layer 504", arranged over the hump 517, between this and a hydrophobic first layer 514 of the liquid-pervious first side 502. The absorption layer 504" consists of a hydrophilic material with good coherence, and with the ability to rapidly acquire and absorb body fluid. Useful absorption materials are for example hydrophilic, absorbent nonwoven materials, tissue layers, or air-laid, bonded cellulose layers. Such materials rapidly absorb liquid and retain part of the liquid inside the material, so that this remains moist or wet after wetting.

The hydrophobic, liquid-pervious surface layer 514 is provided with an opening 520 at the wetting region 515 of the sanitary napkin. Thereby, the absorption layer 504", located inside the liquid-pervious surface layer 514, is exposed through the opening. During the use of the sanitary napkin 501, emitted body fluid will be absorbed directly by the absorption material in the absorption layer 504" at the wetting region 515. In this way, it is prevented that liquid flows out onto the liquid-pervious surface layer 514 of the sanitary napkin and causes leakage.

Furthermore, it is avoided that liquid remains in the first side 502 and is smeared out across the surface thereof and onto the body of the user. Since the second part 504" of the absorbent body has the ability to absorb liquid, this implies that liquid which is emitted to the surface of the layer is absorbed into the layer 504" instead of being left on the surface. By means of absorbing body fluid, the absorption layer 504" becomes wet, or moist, since part of the liquid is retained in the layer. Thereby, the absorption layer 504" exhibits a moist, or wet surface bearing on the body of the user in the wetting region 515. As earlier mentioned, this is a significant advantage since the upper part of the hump 517 of the sanitary napkin 501 reaches in between the labia pudendi of the user and comes into contact with the sensitive mucous membranes in the genital region of the user, are thus protected against desiccation and irritation.

FIG. 6 shows a cross-section through the sanitary napkin 501, shown in FIG. 5. As is clearly evident from FIG. 6, the side edges 509, 510 of the sanitary napkin are bent in a direction downwards-inwards. This implies that the sanitary napkin, along the side edges 109, 100, exhibits rounded ridges 525, 526 which during the use of the sanitary napkin are intended to bear on the body of the user, in the groin folds of the user. The rounded ridges 525, 526 extend along the side edges 509, 510 along almost the entire length of the sanitary napkin, but level somewhat at the front edge 511 and the rear edge 512, respectively.

FIG. 6 shows a cross-section through the sanitary napkin 501, shown in FIG. 5. As is clearly evident from FIG. 6, the side edges 509, 510 of the sanitary napkin are bent in a direction downwards-inwards, seen from the liquid-pervious surface layer 502. This implies that the sanitary napkin, along the side edges 109, 110, exhibits rounded ridges 525, 526 which during the use of the sanitary napkin are intended to bear on the body of the user, in the groin folds of the user. The rounded ridges 525, 526 extend along the side edges 509, 510 along almost the entire length of the sanitary napkin, but level somewhat at the front edge 511 and the rear edge 512, respectively.

In order to further increase the comfort to the user, the front portion 506 is provided with a recess 522 at the front edge 511. The recess 522 is formed by means of the front edge 511 being curved in a direction inwards, towards the crotch portion 508 of the sanitary napkin. Since the crotch edge 506 is concavely-curved, it follows the outline of the mons veneris of the user in a better way, whereby the risk of chafing is almost non-existent.

The body-adapted, anatomically correct shape of the sanitary napkin, means that the sanitary napkin is kept safely and comfortably in position during use, without the need for special attachment members. Several factors influence the good attachment, such as the shape and the location of the hump, the two-dimensional shape of the sanitary napkin which is adapted to the available space between the legs of the user and which prevents the sanitary napkin from sliding backwards during use, the stiff shape-permanent liquid-pervious layer, and the longitudinal curvature according t the curvature on the body of the user. Because of the anatomically adapted shape, the sanitary napkin will always be correctly positioned in relation to the body of the user during use, so that the absorbent material in the wetting region 515 of the sanitary napkin always will be the portion of the sanitary napkin which first is subjected to wetting, and which bears on the mucous membranes of the user during use. The parts of the first side 502 of the sanitary napkin which are in contact with the skin of the user during use, on the other hand, are hydrophobic, which ensures that the skin is kept dry during use. A contributing reason for this is that the surface layer first side 502 prevents rewetting by liquid which has been absorbed into the absorbent body 504 of the sanitary napkin.

The invention should not be regarded as being limited to the herein described embodiments, but a number of further variants and modifications are conceivable within the scope of the claims. For instance, the invention includes all types of absorbent articles for female users, which articles have a part which during use may come into contact with the mucous membranes of the user in the genital region, and a part which is in contact with skin during use. Furthermore, all conceivable combinations of the described embodiments are intended to be included by the invention.

The invention claimed is:

1. Absorbent article for maintaining mucous membranes of a user moist, the absorbent article comprising:
   a liquid-pervious user-facing first side including a first portion consisting of a hydrophobic material, and a second portion forming a wetting region adapted to be disposed adjacent the mucous membranes of the user, to define the region of the first side to first be wetted by body fluid emitted to the article,
   a second side opposite the first side and including a liquid-impervious surface layer, and
   an absorbent body disposed between the first and second sides,
   wherein the second portion consists of hydrophilic absorbent material that is adapted to retain moisture,
   an outer edge of the second portion being bordered by the hydrophobic material of the first portion, wherein an extent of the second portion is smaller than an extent of the absorbent body,
   wherein the second portion is hump-shaped so as to project past the first portion in the direction of a user.

2. A method for maintaining a mucous membrane of a user moist with an absorbent article, the absorbent article including an absorbent body, a user-facing liquid-pervious first side which includes a first portion and a second portion, the article further including a second side opposite the first side and having a liquid impervious layer, the first portion formed of a hydrophobic material, and the second portion formed of a hydrophilic absorbent material, the second portion arranged to be first wetted by body fluid, the absorbent body being disposed between the first and second sides, the method comprising:
   wearing the absorbent article such that the second portion is adjacent the mucous membrane of the user and first receives body fluids emitted from the user;
   retaining at least a portion of the body fluids in the hydrophilic absorbent material of the second portion; and
   maintaining the mucous membrane of the user moist with the body fluids retaining in the hydrophilic absorbent material of the second portion,
   wherein an extent of the second portion is smaller than an extent of the absorbent body; and
   wherein the second portion is hump-shaped so as to project past the first portion in the direction of the user.

3. Absorbent article for maintaining mucous membranes of a user moist, the absorbent article comprising:
   a user-facing liquid-pervious first side including a first portion consisting of hydrophobic material, and a second portion forming a wetting region adapted to be disposed adjacent the mucous membranes of the user, to define the region of the first side intended to first be wetted by body fluid emitted to the article,
   a second side opposite the first side and including a liquid-impervious surface layer, and
   an absorbent body disposed between the first and second sides,
   wherein the second portion consists of hydrophilic absorbent material that is adapted to retain moisture, so as to maintain the mucous membranes of the user moist, an outer edge portion of the second portion being bordered by the hydrophobic material of the first portion which is situated laterally outwardly of the second portion and overlies the absorbent body, wherein the second portion is hump-shaped so as to project past the first portion in the direction of the user.

* * * * *